(12) United States Patent
König et al.

(10) Patent No.: US 8,333,809 B2
(45) Date of Patent: Dec. 18, 2012

(54) METHOD OF PURIFYING IONIC LIQUIDS

(75) Inventors: Axel König, Herzogenaurach (DE); Manfred Stepanski, Buchs (CH); Andrzej Kuszlik, Buchs (CH)

(73) Assignee: Sulzer Chemtech AG, Winterthur (CH)

( * ) Notice: Subject to any disclaimer, the term of this patent is extended or adjusted under 35 U.S.C. 154(b) by 983 days.

(21) Appl. No.: 12/310,100

(22) PCT Filed: Sep. 12, 2007

(86) PCT No.: PCT/CH2007/000445
§ 371 (c)(1),
(2), (4) Date: Feb. 10, 2009

(87) PCT Pub. No.: WO2008/031246
PCT Pub. Date: Mar. 20, 2008

(65) Prior Publication Data
US 2011/0259043 A1    Oct. 27, 2011

(30) Foreign Application Priority Data

Sep. 12, 2006 (CH) .................................. 1457/06

(51) Int. Cl.
*B01D 9/00* (2006.01)
(52) U.S. Cl. ........................................ 23/295 R; 23/300
(58) Field of Classification Search ................ 23/293 R, 23/295 R, 300, 301
See application file for complete search history.

(56) References Cited

FOREIGN PATENT DOCUMENTS

| | | |
|---|---|---|
| DE | 10 2004 027196 | 12/2005 |
| DE | 10 2004 058907 | 6/2006 |
| EP | 0 491 558 A2 | 6/1992 |
| WO | WO 2006/045795 | 5/2006 |

*Primary Examiner* — Edward Johnson
(74) *Attorney, Agent, or Firm* — Francis C. Hand; Carella, Byrne, Et. Al

(57) ABSTRACT

The present invention relates to a method for the purification of an ionic liquid by means of fractional crystallization in which a part of the ionic liquid is crystallized and the crystallizate formed is separated from the liquid remainder. In this respect the ionic liquid is charged with a certain amount of at least one entrainer substance.

23 Claims, 1 Drawing Sheet

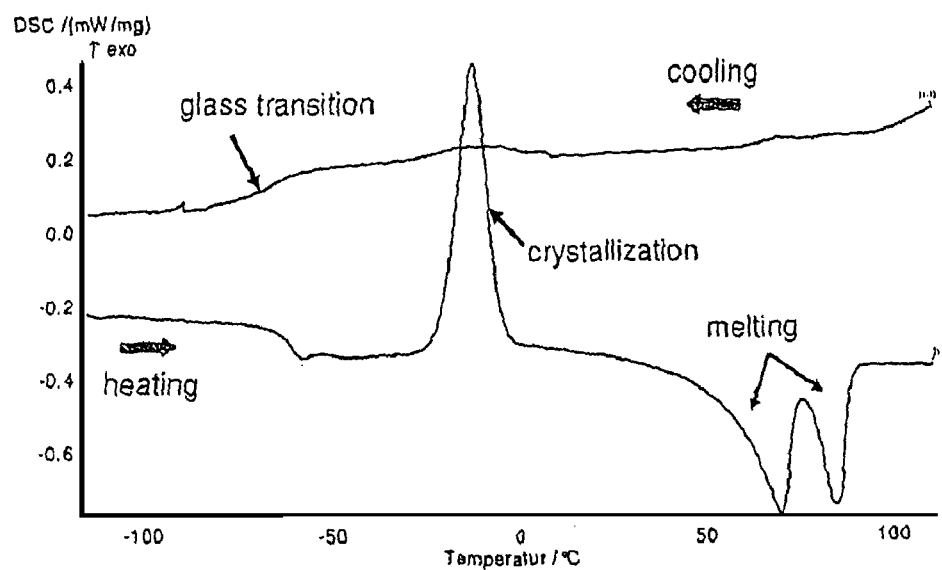

METHOD OF PURIFYING IONIC LIQUIDS

AREA OF THE INVENTION

The present invention relates to a method for the purification of ionic liquids. More particularly, this invention relates to a method for the purification of an ionic liquid by means of fractional crystallization.

PRIOR ART

WO 2006/061188 teaches that for the purification of an ionic liquid, to partially crystallize the melt of the ionic liquid and to separate the crystallizate formed during the crystallization from the residual melt. The crystallization can in this respect be carried out dynamically or statically. In accordance with WO 2006/061188 all types of known ionic liquids can be purified by means of partial crystallization.

DE-A-10 2004 027 196 relates to a method for the crystallization of polymers and biopolymers with a molecular weight of >1000 g/mol with the aid of ionic liquids. In accordance with the method of DE-A-10 2004 027 196 the polymers and the biopolymers are dissolved in a solvent mixture, of which one or more of the solvents are ionic liquids. The fraction of ionic liquid is more than 50 percent of the volume or preferably more than 80 percent of the volume. Now, to achieve the crystallization of the desired polymers or biopolymers, the basis of the method is to change their solubility in the solvent mixture. In this respect, in accordance with a first variant, a saturated solution of a compound to be crystallized is produced in an ionic liquid. This solution is brought into a gaseous volume which contains a specific concentration of a flocculation agent. Over the course of time the solution now slowly saturates out of the gaseous volume with the flocculation agent until the equilibrium is reached. If the equilibrium concentration of the flocculation agent in the ionic liquid is sufficient for precipitation, then crystals of the polymers or biopolymers to be crystallined are found in the ionic liquid.

In accordance with a second variant the polymer to be crystallized is poorly soluble in the ionic liquid; however, it is sufficiently soluble with a cosolvent mixable with the ionic liquid. The polymer is now dissolved in a mixture of ionic liquid and cosolvent and a saturated solution is produced. This mixture is now brought into the gaseous volume which is poor in gaseous cosolvents. The cosolvent slowly evaporates from the mixture containing the ionic liquid and leaves behind an ionic liquid with crystals of the desired polymer. The aforementioned method does not deal with the purification of ionic liquids, but rather with the purification of polymers using ionic liquids. These are present in a liquid aggregate state during the complete method.

A known problem of ionic liquids is that they are generally reluctant to crystallize, since they have a high degree of asymmetry. This hinders crystallization or makes it impossible. Also, many ionic liquids show a complex phase behaviour. The consequence thereof is that many ionic liquids form glass-like structures on cooling. Ionic liquids often possess a high viscosity and furthermore, tend to a strong reduction in temperature up to a glass-like solidification.

Some ionic liquids such as the EMIM-chloride form two crystal modifications of which the higher melting modification is the crystal form more favourable for the separation. With a tendency to a strong reduction in temperature no crystals are formed below the solidification point of the higher melting modification. Only after the transition temperature does the lower melting modification start to crystallize.

Only after falling below the phase transition temperature does the lower melting modification start to crystallize. In extreme cases the formation of crystals does not occur at all during the cooling down even if the temperature was reduced considerably below the phase transition temperature. Such a liquid then solidifies amorphously.

With a high viscosity of the liquid the molecular material transport occurs slowly, whereby very small crystals grow. Such a growth is disadvantageous for the subsequent separation of crystals and residual melt. Such an unfavourable growth can be prevented by a slowing down the growth rate of the crystals in that the liquid is cooled more slowly. However, this is principally unwanted in industrial processes.

In the scope of the present invention salts with organic compounds should be understood as ionic liquids, which should be present in a liquid state below 150° C. and preferably below 100° C. In WO 2006/061188 and DE-A-10 2004 027 196 a large number of possible ionic compounds are listed. The contents of WO 2006/061188 and DE-A-10 2004 027 196 are therefore included by reference in the present application.

OBJECT OF THE INVENTION

Based on this prior art the object of the invention is to provide an improved purification process for ionic liquids which largely excludes the aforementioned disadvantages. A further object of the invention is to provide an improved purification method with which compounds which crystallize in different modifications can be purified more efficiently.

In accordance with the invention, this object is satisfied by a method for the purification of an ionic liquid by means of fractional crystallization in which a.] a part of the ionic liquid is crystallized by the reduction of temperature and b.] the formed crystallizate is separated from the liquid remainder and characterized in that the ionic is first charged with a certain amount of at least one entrainer substance and is only then crystallized. Generally, a carrier substance is to be understood as the entrainer substance which positively influences the distribution of the unwanted components between the solid and the liquid phase in the sense of the separation process. The specific addition of entrainer substances also has the advantage that the viscosity of the liquid (melt) can be reduced and thereby the material transport is intensified (both by diffusion and convection). The separation effect is thereby intensified in that for a given growth rate bigger crystals are produced which leads to a substantially better separation of solid/liquid.

Advantageously a compound is used as an entrainer substance which has similar structural properties to the ionic liquid or to the contaminants contained in the ionic liquid. For example, on the crystallization of EMIM-chloride (1-ethyl-3-methyl-imidazolium-chloride) 1-methylimidazol can be added. The distribution of the contaminants can thereby be positively influenced between the liquid (melt) and the crystallizate. This expresses itself in that less contamination is introduced into the crystallizate.

Advantageously a compound is used as an entrainer substance which has structural properties similar to the contaminants contained in the ionic liquid. The specific addition of such an entrainer substance has the advantage that, for example, the solubility of the contaminants is increased and they thereby increasingly remain in the liquid. Generally, a mixture of compounds (carrier substances) can also be added as the carrier substance.

Advantageously the quantity by weight of the entrainer substance added to the contaminated ionic liquid is less than 50 per cent per weight of the ionic liquid, preferably less than 30 per cent per weight of the ionic liquid and in particular preferably less than 10 per cent per weight of the ionic liquid. This means in practice that the person of ordinary skill in the art will generally only add such an amount of an entrainer substance for which the desired improvement of the solubility of the contaminants and/or generally the desired increase in the separation effect is achieved. Due to the addition of an entrainer substance the melting point of the ionic liquid is generally lowered such that, under some circumstances, more energy is required for the carrying out of the crystallization process.

It should be understood by similar structural properties that the entrainer substance, for example, has the same basic structure as the ionic liquid or a similar polarity so that its solubility is improved, but, it is itself typically not ionic.

Known classical solvents can also be used as an entrainer substance which have similar structural properties to the contaminants contained in the ionic liquid to be purified. The solvents which come into consideration are, for example: methanol, ethanol, i-propanol, butanol, pentane, hexane, acetone, methyl-ethyl-ketone, furan, dimethyl-sulfoxide, toluene, benzene, methyl acetate, ethyl acetate, or a mixture of one or more of the above named solvents.

Advantageously the crystallization is carried out in positive pressure and gases soluble in the ionic liquid such as $CO_2$, $CH_4$, and $N_2$ are used as the carrier substance. The use of soluble gases has the advantage that the gases can be easily expelled again. It is also conceivable to use condensable gases such as methane, ethane, propane, n-butane or halogenated hydrocarbons such as chloromethane as the entrainer substance in the ionic liquid. Also, these gases can easily be expelled again at a slightly increased temperature.

Entrainer substances can be used for the static crystallization and for the dynamic crystallization of ionic liquids. On static crystallization no externally enforced convection of the liquid phase takes place and the crystals form on cooled surfaces which are arranged in the crystallizer.

On dynamic crystallization the liquid phase is stirred or circulated. Known dynamic crystallization methods are: Suspension crystallization, crystallization of the complete flowed-through tube type or falling film crystallization. The previously mentioned methods of crystallization are more closely described in U.S. Pat. No. 5,504,247 and WO 2006/061188 whose content is hereby included by reference.

Principally a one step or a multiple step method of crystallization can be used for the purification of the ionic liquid. Advantageously the crystallization is carried out in multiple steps as fractional crystallization. The individual crystallization levels define different degrees of purity of the desired compound. In the lowest crystallization level the contaminants are of the highest concentration; in the highest crystallization level the desired compound is present in the purified form in which the contaminants are depleted the most. In the multiple step method of crystallization the non crystallized residue of a. crystallization level is fed into the next lower crystallization level. The precipitated crystals of a crystallization level are preferably sweated and the captured sweating phase is re-fed into the operating mixture of the same level or it is separated into two fractions of which the first fraction is added to the residue of the crystallization level and the second fraction is added to the feed mixture of the same level. The remaining crystallizate is then melted and added to the next higher crystallization level. Basically an arbitrary number of crystallization levels can be ordered next to one another. So many crystallization levels are used in practice that the crystallizate of the highest crystallization level has the desired purity.

The contaminants are enriched in the residue of the lowest crystallization level. In the present case the residue contains the entrainer substances together with other contaminants.

EMBODIMENTS

The effectiveness of the purification of chlorides or bromides of 1-ethyl-3-methyl-imidazolium, 1-butyl-3-methyl-imidazolium, 1-hexyl-3-methyl-imidazolium or 1-octyl-3-methyl-imidazolium can be increased through the addition of 1-methyl-imidazole as an entrainer substance. The structural similarity is present here between the imidazole rings of the entrainer substance and the imidazole cations. A similar effect is, however, also achieved through the addition of, for example, octane which as an entrainer substance has a structural affinity to the ethyl groups, butyl groups, hexyl groups or octyl groups of the above named ionic compounds. Further examples are chlorides or bromides of ethyl-pyridinium and methyl-pyridinium whose purification is increased through the addition of pyridine. A further example is an ionic liquid consisting of imidazolium as a cation and toluene-sulphate as an anion, whose purification effect can be increased through the addition of benzene, xylene, toluene or a mixture of such substances. In this example the entrainer substances have a structural similarity to the toluene sulphate anions.

The invention also provides a method that is characterized in that the liquid or a part of the liquid mass is cooled down to such an extent that the lower melting modification crystallizes, in that the crystallizate of the lower melting modification is subsequently heated to such an extent that the lower melting modification is converted into a different higher melting modification and in that the seeds in the thus generated higher melting modification are used for the consequent crystallization. It was surprisingly found that the reheating of an initially named, mass solidified in glass like form, a crystallization of the lower melting modification can still begin below the phase transition temperature. The crystals are therefore not produced on cooling, but, only on the heating after a glass like solidification. The method in accordance with the invention has the advantage that the complete solid mass is subsequently crystallized in the modification favourably for the purification. In a variant of this method the liquid or a part of the liquid mass is cooled to such an extent that a glass like solidification occurs and as a consequence subsequently the thus cooled mass undergoes a heating, with the lower melting modification still crystallizing below the phase transition temperature on such a heating.

Advantageously the lower melting modification is brought to crystallization through a cooling below the transition point and subsequent heating. It can thereby be achieved that the component to be obtained crystallizes in the desired crystal modification. The method in accordance with the invention can be used for any compound which tends to cooling and for which the more appropriate modification for the purification can be achieved by a transition of a less appropriate modification.

The invention will be described in more detail in the following with reference to the enclosed diagram 1 which illustrates the differential scanning calorimetry of EMIM-chloride.

The diagram shows the cooling curves and the heating curves for EMIM-chloride. On cooling from 100° C. to −100° C. no peaks could be identified, which could lead to the conclusion of crystallization. The curve progression leads to the conclusion that an amorphous (glass like) solidification occurred.

On re-heating a large exothermic peak occurs at approximately −10° C. which is achieved by crystallization. At temperatures of approximately 70° C. and 85° C. two endothermic peaks are visible which are produced by modification transitions and melting. In accordance with the invention the heating is aborted prior exceeding the temperature of the second endothermic peak so that the higher melting modification is not melted. This non melted crystal mass then forms the seeds for the subsequent crystallization.

Ionic liquids which are open to a purification in accordance with the method in accordance with the invention are substances, for example, which correspond to the general formula $aA^{m+}bX^{n-}$, with n=1 or n=2 or m=2 and a·m=b·n and the cation being chosen from: quaternary ammonium cations of the general formula

[R'''][N+]([R'])([R''])[R], quaternary phosphonium cations of the general formula

[R'''][P+]([R'])([R''])[R], substituted or un-substituted imidazolium cations of the general formula

[R]N1C=C[N+]([R'])=C1, substituted or un-substituted morpholinium cations of the general formula

[R]N+1CC[O]CC1, substituted or un-substituted oxazolinium cations of the general formula

[R]N+1=COCC1, substituted or un-substituted pyridinium cations of the general formula

[R]N+1=CC=CC=C1, substituted or un-substituted pyrrolidinium cations of the general formula

[R]N+1([R']CCCC1, substituted or un-substituted pyrazolinium cations of the general formula

[R]N+1C=CCC=N1 substituted or un-substituted triazolium cations of the general formula

[R]N+1([R'])N=CC=N1 or

[R]N+]1([R'])C=NC=N1, substituted or un-substituted guanidinium cations of the general formula

[R']N([R])C(N([R''])[R'])=[N+]([R'''])[R''']

and the anion is chosen from the group consisting of halogenides, tetra-fluoro-borate, RBF3—, hexa-fluoro-phosphate, RRR'PF₃—, phosphate, PR'PO₄—, dicyanamide, carboxylate R—COO—sulphonate R—SO₃—, benzenesulfonic acid, p-toluenesulphonic acid, organic sulphates R—O—SO₃—, bsi(sulphone)imides R—SO₂—N—SO₂—R', imides of the structure [R]S([N—]) C([R])=O)(=O)=O/SCN—, CN—, nitrate, nitrite, chlorate, perchlorate, with R and R' being able to be either a linear or a branched 1 to 20 carbon atom containing aliphatic alkyl or alicyclic alkyl or a C5-C15-aryl-C5-C15-aryl-C1-C6-alkyl- or C1-C6-alkyl-C5-C15-aryl-remainder independently of one another which can be substituted by halogen atoms and/or hydroxyl groups.

The invention claimed is:

1. A method for the purification of an ionic liquid by means of fractional crystallization wherein the ionic liquid is a salt of an organic compound which is present in a liquid state below 150° C. and in which
   a.] a part of the ionic liquid is crystallized by the reduction of temperature and
   b.] the formed crystallizate is separated from the liquid remainder, characterized in that the ionic liquid is first charged with a certain amount of at least one entrainer substance and is then crystallized so that the solubility of contaminants is increased and thereby the contaminants increasingly remain in the liquid.

2. A method in accordance with claim 1, characterized in that a compound is used as an entrainer substance which has similar structural properties to the ionic liquid.

3. A method in accordance with claim 1, characterized in that a compound is used as an entrainer substance which has structural properties similar to contaminants contained in the ionic liquid.

4. A method in accordance with claim 1 characterized in that the quantity by weight of the entrainer substance added to the contaminated ionic liquid is less than 50 per cent per weight, preferably less than 30 per cent per weight and in particular preferably less than 10 per cent per weight.

5. A method in accordance with claim 1 characterized in that known classical solvents are used as an entrainer substance which have similar structural properties to the ionic liquid containing contaminants which is to be purified.

6. A method in accordance with claim 1 characterized in that said entrainer substance is at least one of methanol, ethanol, i-propanol, butanol, pentane, hexane, acetone, methyl-ethyl-ketone, tetra hydro-furan, dimethyl-sulfoxide, toluene, benzene, methyl acetate, ethyl acetate and a mixture of one or more thereof.

7. A method in accordance with claim 1 characterized in that the crystallization is carried out in positive pressure and in that said entrainer substance is at least one of $CO_2$, $CH_4$ and $N_2$.

8. A method in accordance with claim 1 characterized in that said entrainer substance is a condensable gas selected form the group consisting of methane, ethane, propane, n-butane and short chained halogenated hydrocarbons.

9. A method in accordance with claim 1 characterized in that the crystallization is carried out dynamically.

10. A method in accordance with claim 1 characterized in that the crystallization is carried out statically.

11. A method in accordance with claim 1 characterized in that the crystallization is carried out as layer crystallization.

12. A method in accordance with claim 1 characterized in that the crystallization is carried out as suspension crystallization.

13. A method in accordance with claim 1 characterized in that a combination of different crystallization methods is used.

14. A method in accordance with claim 1 characterized in that a combination of static and dynamic layer crystallization of the falling film type are used.

15. A method in accordance with claim 1 characterized in that the crystallizate is sweated.

16. A method in accordance with claim 1 characterized in that the crystallization is carried out in multiple steps.

17. A method for the purification by means of fractional crystallization of a substance present in liquid form which forms as a solid at least two different crystal modifications at different temperatures and tends to cool in which,
- a.) a part of the substance is precipitated as a crystallizate and
- b.) the formed crystallizate is separated from the liquid remainder, characterized in that the liquid or a part of the liquid mass has cooled down so far that the low melting modification crystallizes, in that the low melting modification is subsequently heated to such an extent that the low melting modification is changed into a different higher melting modification and in that the seeds in the so generated higher melting modification are used for the consequent crystallization.

18. A method in accordance with claim 17, characterized in that through cooling below the transition point and consequent heating the low melting modification is made to crystallize out.

19. A method in accordance with claim 17 characterized in that such a generation of seeds is carried out in one of a static crystallizer and a dynamic crystallizer.

20. A method in accordance with claim 17 characterized in that said substance is an ionic liquid.

21. A method in accordance with claim 17 characterized in that a combination of static layer crystallization and dynamic layer crystallization of the falling film type are used.

22. A method in accordance with claim 17 in that the crystallizate is sweated.

23. A method in accordance with claim 17 characterized in that the crystallization is carried out in multiple steps.

* * * * *